(12) United States Patent
Zhang et al.

(10) Patent No.: US 11,104,879 B1
(45) Date of Patent: *Aug. 31, 2021

(54) **SANXAN GUM SYNTHETIC STRAIN-*SPHINGOMONAS* SP. WITH A MOLECULAR MARKER AND APPLICATION THEREOF IN SANXAN GUM PREPARATION**

(71) Applicant: HEBEI XINHE BIOCHEMICAL CO., LTD., Xingtai (CN)

(72) Inventors: Yu Zhang, Xingtai (CN); Guopei Zhang, Jizhou (CN); Shaohua Zhang, Xingtai (CN)

(73) Assignee: HEBEI XINHE BIOCHEMICAL CO., LTD., Xingtai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/984,776

(22) Filed: Aug. 4, 2020

(30) Foreign Application Priority Data

Apr. 27, 2020  (CN) .......................... 202010346509.7

(51) Int. Cl.
*C12N 1/20* (2006.01)
*C12P 19/06* (2006.01)
*C12R 1/01* (2006.01)

(52) U.S. Cl.
CPC ............... *C12N 1/20* (2013.01); *C12N 1/205* (2021.05); *C12P 19/06* (2013.01); *C12R 2001/01* (2021.05)

(58) Field of Classification Search
CPC ....................................................... C12N 1/20
See application file for complete search history.

*Primary Examiner* — Yong D Pak
(74) *Attorney, Agent, or Firm* — CBM Patent Consulting, LLC

(57) ABSTRACT

The present invention relates to Sanxan gum preparation, and more particularly to a Sanxan gum synthetic strain-*Sphingomonas* sp. with a molecular marker and application thereof in Sanxan gum preparation by inoculating the *Sphingomonas* sp. strain (CGMCC No. 19480) into a culture medium containing a carbon source and a nitrogen source after sterilization, aeration fermentation and extraction. The invention solves the problems of no rapid identification of a product containing Sanxan gum and synthetic strain, and low performance indexes of a prepared Sanxan gum. It can quickly identify whether a product contains Sanxan gum. The main technical indicators of the prepared Sanxan gum products are significantly better than the existing products.

16 Claims, 2 Drawing Sheets
Specification includes a Sequence Listing.

Figure 2:
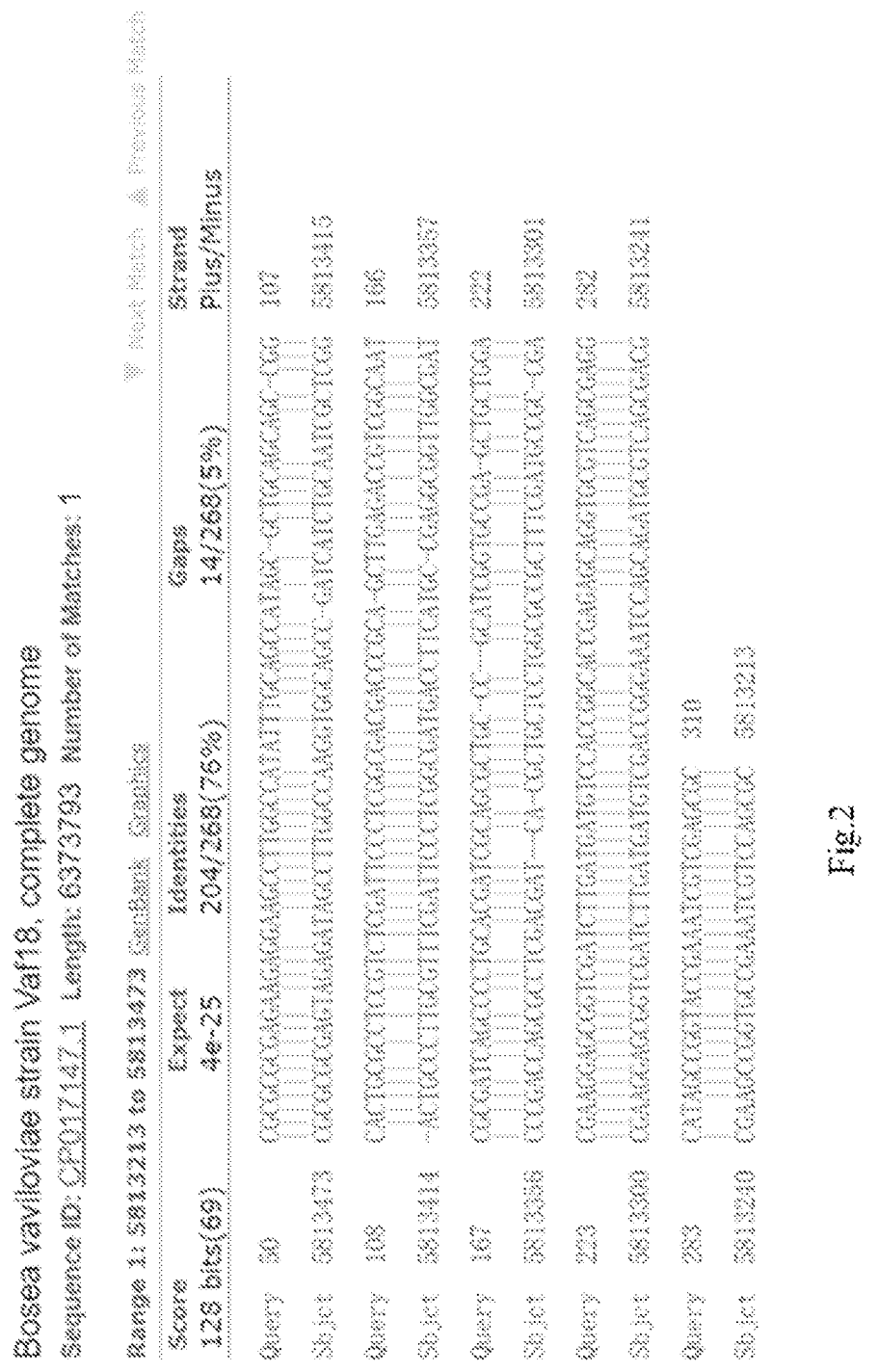

Fig. 2

SANXAN GUM SYNTHETIC STRAIN-*SPHINGOMONAS* SP. WITH A MOLECULAR MARKER AND APPLICATION THEREOF IN SANXAN GUM PREPARATION

TECHNICAL FIELD

The present invention relates to the field of preparation of Sanxan gum, and more particularly to a Sanxan gum synthetic strain-*Sphingomonas* sp. with a molecular marker and an application thereof in Sanxan gum preparation.

BACKGROUND

Sanxan gum is also known as sphingan Ss, which is a new type of microbial glue synthesized by *Sphingomonas sanxanigenens*. It exhibits excellent thickening, gelatinizing, emulsifying and suspending stabilizing properties. It is a new variety of sphingan polymers, and is also the first microbial-derived food gum that has been independently developed and industrialized in China. Sanxan gum has passed the technical examination of the Expert Evaluation Committee of the National Health Commission according to the "Regulations on the Application and Acceptance of New Food Additive Varieties" and the "Management Method on New Food Additive Varieties" in December 2018. It is mainly used as a thickener, stabilizer and coagulant in fruit and vegetable juice (pulp) drinks, vegetable protein drinks, meat enema and other products.

For the Sanxan gum in microbial gum (especially the Sanxan gum independently developed in China), there is a need for a method to identify Sanxan gum and its synthetic strain from the perspective of protection and application market regulation of production strains. With the application and promotion of Sanxan gum, it is an urgent problem to regulate the product application market and identify whether the Sanxan gum is added to a product.

At present, the industrial production of the Sanxan gum is as follows. The *Sphingomonas* sp. is used as a production strain, and the glucose and inorganic nitrogen source are used as the main raw materials. It is prepared by fermentation, extraction, drying and other processes using biological and chemical technology.

The patent application No. 200610048338.X has disclosed a *Sphingomonas* sp. and a method for producing microbial polysaccharides using it. The method includes preparing Sanxan gum fermentation broth by using *Sphingomonas* sp. (CGMCC No. 1650) as a strain and using glucose or sucrose medium as a carbon source under the conditions of aeration volume of 0.2 vvm-0.5 vvm, stirring speed of 120-160 rpm, culture temperature of 35-40° C., and fermentation period of 60-70 hours; then adjusting isoelectric point of the fermentation broth with soluble neutral salt; and performing sedimentation, extraction and dehydration to obtain microbial polysaccharide Sanxan gum. The yield of Sanxan gum in the above method is about 18 g/L, the viscosity of 1% KCl solution of the Sanxan gum is 1200 MPa·s, the viscosity of 0.25% synthetic brine of the Sanxan gum is 300 MPa·s, the viscosity of 1% aqueous solution of the Sanxan gum is 600 MPa·s, and the gel strength of the Sanxan gum is about 18 g/cm².

With increasing application of Sanxan gum and improvement of its product performance requirements, effectively reducing production cost of the Sanxan gum, improving fermentation yield of the Sanxan gum, and improving performance indicators of its products including viscosity of 1% KCl solution and viscosity of 0.25% synthetic brine, viscosity of 1% aqueous solution, and gel strength are not only the actual demand for expanding industrial application of the Sanxan gum, but also are one of the research hotspots in this field.

SUMMARY

An object of the present invention is to provide a Sanxan gum synthetic strain-*Sphingomonas* sp. with a molecular marker.

Another object of the present invention is to provide an application of the Sanxan gum synthetic strain-*Sphingomonas* sp. with a molecular marker in Sanxan gum preparation.

The overall technical solution of the present invention is:

a Sanxan gum synthetic strain-*Sphingomonas* sp. with a molecular marker has a deposit number of CGMCC No. 19480, Latin name of *Sphingomonas* sp., and the molecular marker is a nucleotide sequence shown in SEQ ID NO: 1.

The strain of the present invention with Latin name of *Sphingomonas* sp. has been deposited in China General Microbiological Culture Collection Center (CGMCC) with the address of Institute of Microbiology, Chinese Academy of Sciences, No. 3, No. 1 yard, Beichen West Road, Chaoyang District, Beijing, the depositary date of the strain is Mar. 16, 2020, and the deposit number is CGMCC No. 19480.

The strain of the present invention is obtained by mutation of *Sphingomonas* sp. (CGMCC No. 1650). The colony of the strain shows round shape, white color, and uplift. The diameter of the colony is 0.3 mm-0.5 mm when culturing at 28-32° C. for 100 hours, and the morphology of the strain is *bacillus* and irregular arrangement. The Sanxan gum synthesized by the strain exhibits good viscosity and gel properties.

The application of the Sanxan gum synthetic strain-*Sphingomonas* sp. with a molecular marker in Sanxan gum preparation.

The specific technical solution of the present invention also includes the following aspects.

The application of the Sanxan gum synthetic strain-*Sphingomonas* sp. with a molecular marker in Sanxan gum preparation, includes the steps of:

A, inoculating the *Sphingomonas* sp. strain (CGMCC No. 19480) into a culture medium containing a carbon source and a nitrogen source after sterilization;

B, performing aeration fermentation at 28-32° C. until fermentation broth viscosity is not less than 3000 cp and residual sugar does not exceed 0.3%;

C, performing extraction of the fermentation broth, solid-liquid separation, neutralization, drying and crushing to obtain the Sanxan gum.

In order to facilitate the growth of the strain and the synthesis of the final product, the preferred technical solution is that the carbon source in the culture medium of the step A is selected from one or any combination of sucrose, glucose, corn powdered sugar, and starch hydrolyzed sugar; and the nitrogen source is selected from one or any combination of peptone, yeast extract, sodium nitrate, ammonium chloride, and ammonium sulfate.

In order to facilitate the growth of the strain and to realize industrial fermentation and control the fermentation cycle, the preferred technical solution is that, in the step A, the *Sphingomonas* sp. strain (CGMCC No. 19480) is inoculated into the culture medium in a fermentation tank with an inoculation amount in which the volume percentage of the seed liquid and the culture medium is 10%-20%.

In order to facilitate the growth of the strain and the synthesis of the final product, the culture medium in the step A is composed of the following components in mass percentage: carbon source 40%-60%; nitrogen source 3%-5%; magnesium sulfate 1%-2%; dipotassium hydrogen phosphate 3%-4%; soluble ferrous salt 3-5 ppm; calcium carbonate 1%-3%; GPe 0.3%-0.5%; and water as balance, pH=7.0-7.2.

In order to realize industrial production of the Sanxan gum, the preferred technical solution is that, in the step A, the *Sphingomonas* sp. strain (CGMCC No. 19480) after amplification culture is inoculated into the culture medium with an inoculation amount in which the volume percentage of the seed liquid and the culture medium is 10%-20%.

The preferred technical solution is that the amplification culture process including the steps of:

inoculating the *Sphingomonas* sp. strain (CGMCC No. 19480) into a first-class seed culture medium to obtain first-class seeds by aeration culture;

performing amplification culture of the first-class seeds to obtain second-class seeds;

inoculating the second-class seeds into the culture medium with an inoculation amount in which the volume percentage of the second-class seeds and the fermentation culture medium is 10%-20% to perform aeration fermentation.

Preferably, The process conditions for obtaining the first-class seeds in the step (1) of the amplification culture process are as follows: inoculating an agarslant strain into the sterile first-class seed culture medium according to an inoculation amount of 0.5%-0.8% mass ratio, performing aeration culture to obtain the first-class seeds under conditions of culture temperature of 28-32° C., aeration volume of 0.4 vvm-0.6 vvm, seed age of 20-24 hours. The conditions for seed transmitting are *bacillus* strain, irregular arrangement and no pollution under microscopic examination.

An agarslant strain culture medium per liter includes the following components: 1.2 g sucrose; 0.25 g peptone; 0.25 g dipotassium hydrogen phosphate; 0.15 g yeast powder; 0.15 g diammonium hydrogen phosphate; 0.01 g magnesium sulfate; and 20 g agar; pH=7.0-7.2.

The first-class seed culture medium per liter includes the following components: 10-15 g carbon source; 5-8 g nitrogen source; 1-2 g magnesium sulfate; 3-4 g dipotassium hydrogen phosphate; 3-5 ppm soluble ferrous salt; and 0.3-0.5 g GPe; pH=7.0-7.2, wherein the carbon source is selected from one or any combination of sucrose, glucose, corn powdered sugar, and starch hydrolyzed sugar; and the nitrogen source is selected from one or any combination of peptone, yeast extract, sodium nitrate, ammonium chloride, and ammonium sulfate.

Preferably, a second-class seed culture medium in the step (2) of the amplification culture process includes the following components: 10-15 g carbon source; 5-8 g nitrogen source; 1-2 g magnesium sulfate; 3-4 g dipotassium hydrogen phosphate; 3-5 ppm soluble ferrous salt; and 0.3-0.5 g GPe; pH=7.0-7.2, wherein the carbon source is selected from one or any combination of sucrose, glucose, corn powdered sugar, and starch hydrolyzed sugar; and the nitrogen source is selected from one or any combination of peptone, yeast extract, sodium nitrate, ammonium chloride, and ammonium sulfate.

The first-class seeds are inoculated into the sterile second-class seed culture solution with an inoculation amount in which the volume percentage of the first-class seeds and the second-class seed culture solution is 10%-20%. The first-class seeds are cultured to obtain the second-class seeds under conditions of culture temperature of 28-30° C., aeration volume of 0.4 vvm-0.6 vvm, and seed age of 20-24 hours. The conditions for seed transmitting are *bacillus* strain, irregular arrangement and no pollution under microscopic examination.

Preferably, second-class seed culture solution is composed of the following components in mass percentage: glucose 2.5%-2.8%; maltose 1.5%-2.0%; soy powder 0.8%-1.0%; ammonium sulfate 0.2%-0.3%; and sterile water as balance; pH=7.0-7.3;

The first-class seeds are inoculated into the sterile second-class seed culture solution with an inoculation amount in which the volume percentage of the first-class seeds and the second-class seed culture solution is 12%-18%. The first-class seeds are cultured to obtain the second-class seeds under conditions of culture temperature of 30-32° C., aeration volume of 0.9 vvm-1.0 vvm, and culture period of 8-10 hours.

In order to facilitate the growth of the strain and the synthesis of the Sanxan gum, the aeration volume in the step B is 0.6-1.0 vvm.

In order to facilitate the detection of the fermentation broth viscosity to control the fermentation end point, the preferred technical solution is that the detection method of the fermentation broth viscosity in the step B includes:

(1) taking about 50 mL of the fermentation broth, removing its surface and stirring with a glass rod for 2-3 turns;

(2) correcting the leveling of a viscometer: adjusting a screw in its foot to make sure the viscometer is level;

(3) installing a rotor: installing a No. 4 rotor by turning it slightly;

(4) placing a beaker containing the fermentation broth on a lifting platform directly below the rotor, adjusting the lifting platform so that the liquid level of the fermentation broth reaches the scale of the rotor;

(5) turning on the power switch of the viscometer, adjusting the speed of the viscometer to 60 rpm, and reading the value after stabilization, where the viscosity=value×100.

In order to facilitate the extraction of Sanxan gum from the fermentation broth, preferably the extraction step in the step C includes adding acid to adjust pH of the fermentation broth to 1.5-2.0, rising the temperature to 60-80° C. and maintaining for 30-50 minutes. The acid is one or any combination of hydrochloric acid, sulfuric acid, and chloroacetic acid with a volume percentage concentration of 10%.

More preferably, the neutralization step in the step C includes adding fibrous materials to one or a mixture of sodium carbonate, sodium hydroxide and potassium hydroxide so that the pH of the fibrous materials after neutralization is 6.5-7.5 and the fibrous materials after neutralization is uniform and agranular.

The residual sugar in the fermentation broth can be measured by the method described in the existing textbooks or reference books. The method includes the steps of:

(1) sucking 1 mL the fermentation broth with a 2.5 mL needle into a 250 mL triangular beaker;

(2) adding 5 mL distilled water and shaking;

(3) adding 20 mL Fehling reagent with 20 mL pipette into the triangular beaker and shaking;

(4) placing the triangle beaker in the electric furnace for heating, keeping boiling for 1 minute after boiling, and cooling it to room temperature;

(5) adding 15 mL of 2 mol/L sulfuric acid, and shaking;

(6) performing titration with 0.1 mol/L $Na_2S_2O_3$ standard solution until the solution appears light yellow, then adding 1 mL of 1% (w/v) starch indicator, continuing to perform titration until the blue fades to white; reading the consumed volume of $Na_2S_2O_3$ (alternatively, adding 10 mL of $Na_2S_2O_3$ in advance, adding starch indicator, and then performing titration with 0.1 mol/L $Na_2S_2O_3$ standard solution);

(7) calculation: performing subtraction between consumed volume of $Na_2S_2O_3$ by a blank solution and consumed volume of $Na_2S_2O_3$ by a sample, and checking sugar content table (g/100 mL).

In order to verify the process and product performance of the prepared Sanxan gum of the present invention, the applicant conducted the following tests.

One, detection of gum yield, comprising:
(1) weighing 100 g the fermentation broth in beaker;
(2) adding about 200 mL of 5%-10% (v/v) hydrochloric acid solution, stirring with a glass rod to obtain complete sedimentation without slurry wrapping, and squeezing with filter cloth;
(3) placing squeezed materials into a culture dish, shredding and drying under a drying lamp for about 4 hours;
(4) drying at 105° C. in oven to constant weight for about 4 hours, and weighing with a balance to obtain sample weight;
(5) calculation formula: gum yield=(the sample weight× 1.08)/volume×100%

Two, viscosity measurement of 1% potassium chloride solution:
1, instruments and equipment:
analytical balance with measurement precision of 0.001 g; high-speed stirrer; Brookfield viscometer: measurement error ±5%, or other viscometer with an equivalent performance.
2, measurement condition:
rotor model: No. 3 rotor;
rotor speed: 60 rpm; and
measurement temperature: 25±1° C.
3, analysis steps
(1) preparation of a solution containing 1% sample and 1% potassium chloride
weighing 3 g sample and 3 g potassium chloride (precision of 0.001 g) with clean and dry weighing paper, and mixing; adding 300 mL distilled water into a beaker; placing the beaker under a stirrer; stirring at a speed of 8000 rpm; slowly adding the mixed sample into the beaker; starting timing; stirring continuously for 15 minutes; stopping stirring and taking out the beaker; and turning the solution up and down with a stir bar or the like for a few times.
(2) detection
adding the solution containing 1% sample and 1% potassium chloride into a high-type beaker, and detecting under the above detection conditions to obtain viscosity.

Three, viscosity measurement of 0.25% synthetic brine:
1, instruments and equipment:
analytical balance with measurement precision of 0.001 g; high-speed stirrer; Brookfield viscometer: measurement error ±5%, or other viscometer with an equivalent performance.
2, measurement condition:
rotor model: No. 1 rotor;
rotor speed: 3 rpm; and
measurement temperature: 25±1° C.
3, analysis steps
(1) preparation of synthetic brine
weighing 10 g NaCl and 1.11 g $CaCl_2$ into 400 mL distilled water, and performing constant-volume with distilled water to 1000 mL.

(2) preparation of a solution
weighing 1 g sample (precision of 0.001 g) with clean and dry weighing paper, adding 400 mL the synthetic brine into a beaker; placing the beaker under a stirrer, stirring at a speed of 8000 rpm; slowly adding the sample into the beaker; starting timing; stirring continuously for 15 minutes; stopping stirring and taking out the beaker; and turning the solution up and down with a stir bar or the like for a few times.
(3) detection adding the solution into a high-type beaker, and detecting under the above detection conditions to obtain viscosity.

Four, viscosity measurement of 1% aqueous solution:
1, instruments and equipment:
analytical balance with measurement precision of 0.001 g; high-speed stirrer; Brookfield viscometer: measurement error ±5%, or other viscometer with an equivalent performance.
2, measurement condition:
rotor model: No. 3 rotor;
rotor speed: 60 rpm; and
measurement temperature: 25±1° C.
3, analysis steps
(1) preparation of a solution
weighing 3 g sample (precision of 0.001 g) with a clean and dry weighing paper; adding 300 mL distilled water into a beaker; placing the beaker under a stirrer; stirring at a speed of 8000 rpm; slowly adding the mixed sample into the beaker; starting timing; stirring continuously for 15 minutes; stopping stirring and taking out the beaker; and turning the solution up and down with a stir bar or the like for a few times.
(2) detection
adding the 1% aqueous solution into a high-type beaker, and detecting under the above detection conditions to obtain viscosity.

Five, detection of gel strength
1, instruments and equipment:
analytical balance with measurement precision of 0.001 g; thermostat: temperature range of 5–50° C., gel strength tester, water bath kettle: control temperature range of room temperature to 100° C.
2, measurement condition:
probe shape and size: 1.0 square centimeter stainless steel piston cylinder; and probe moving speed: 10 mm/s.
3, analysis steps
(1) preparation of a sample
weighing 3 g sample (precision of 0.001 g), slowly adding the sample into a beaker containing 300 mL distilled water under the condition of being stirred at a speed of 8000 rpm, stirring for 15 minutes, pouring the sample solution into a high-type beaker, heating in a 95° C. water bath kettle, stirring intermittently 3 cycles with a glass rod (5-10 times for each cycle), taking out the beaker after heating for 30 minutes, removing the upper layer of foam, pouring the gum solution into a flat-bottomed container when it is hot with a liquid level of 4 cm, maintaining, and after naturally cooling to gel, putting it in a 20° C. thermostat and maintaining for 20 hours to be tested.
(2) detection
detecting three parallel samples with the gel strength tester to obtain arithmetic mean.

Six, detection of particle size
1, instruments and equipments:
analytical balance with measurement precision of 0.001 g; standard sieve: 80 mesh (0.175 mm bore diameter) sieve;

2, analysis steps weighing 50 g sample (precision of 0.001 g) in an 80 mesh (0.175 mm bore diameter) sieve, immediately manually shaking and slapping the sieve until no sample is dropped, and weighing the quality of sieve residue.

3, result calculation calculating the particle size w according to the following formula:

$$w=(m-n)/m\times 100\%,$$

where m means the sample weight (g), and n means the weight of sieve residue (g).

The results are based on the arithmetic mean of the parallel detection results, and the absolute difference between two independent detection results obtained under repeatability conditions is not more than 2%.

Seven, detection of whiteness 1, principle:

the whiteness of the sample is obtained by comparing reflectivity of the sample to a blue light with that of a standard whiteboard to the blue light under the specified conditions.

2, instruments (1) whiteness meter: the wavelength being adjustable to 457 nanometers, and suitable sample boxes and the standard whiteboard: reading precision of 0.1; and (2) sample pressing machine.

3, operation process (1) pre-treatment of the sample mixing the sample fully;

(2) operation of the whiteness meter performing adjustment of "black" and whiteboard calibration following the instructions of the whiteness meter.

(3) detection pressing two samples to be detected with the sample pressing machine respectively, according to the operation steps of the whiteness meter; performing parallel test of the samples by the whiteness meter; and reading the whiteness values.

(4) result repression i) repression method: expressing the whiteness of the sample with the blue light whiteness measured by the whiteness meter; and using the arithmetic mean value of the parallel tests as the result and reserving a decimal fraction.

ii) repeatability: the absolute difference of the parallel test results should not exceed 0.2; if it exceeds the above value, it should be re-detected.

The present invention comprises at least the following substantive features and significant progress:

1. The present invention screens a specific molecular marker of Sanxan gum and its synthetic strain from the perspective of Sanxan gum synthetic gene clusters and comparative genomes, can identify Sanxan gum from medium-light processed products containing Sanxan gum, and has advantages of short detection time and high accuracy.

2. The present invention screens *Sphingomonas* sp. CGMCC No. 19480 by which the prepared Sanxan gum has high production yield and much better performance than existing strain.

3. The yield of Sanxan gum prepared by the strain of the present invention is higher than that of the existing process. The prepared Sanxan gum has much better performances such as viscosity of 1% KCl solution, viscosity 0.25% synthetic brine, viscosity of 1% aqueous solution, and gel strength than existing Sanxan gum products.

BRIEF DESCRIPTION OF THE DRAWINGS

FIG. 2 is comparison drawing of sequence (SEQ ID NO: 5) of obtained highest homologous species *Bosea vaviloviae* strain Vaf18 and sequence (SEQ ID NO: 4) of the molecular marker of the present invention when a BLASTN alignment is performed between nucleic acid sequences of *Sphingomonas* Sp. CGMCC No. 19480 with those of all species in GenBank database; the SEQ ID NO: 4 is a partial of sequence of SEQ ID NO: 1.

DETAILED DESCRIPTION OF EMBODIMENTS

Figure 1:
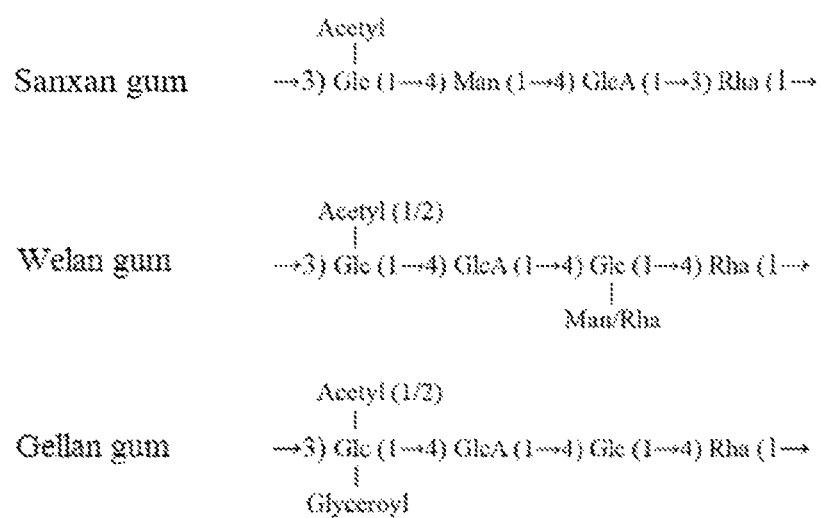
FIG. 1 is a comparison drawing of the polysaccharide structure of Sanxan gum, welan gum, and gellan gum, where Glc is glucose, Man is mannose, GlcA is glucuronic acid, Rha is rhamnose, Acetyl is acetyl group, and Glyceroyl is glyceryl group.

The present invention will be described in further detail with reference to the embodiments and the accompanying drawings below. However, the embodiments and the accompanying drawings are not intended to limit the present invention. The scope of protection of the present invention is based on the contents recited in the claims. Any replacement of equivalent technical means based on the description will not deviate from the protection scope of the present invention. The methods that do not indicate specific conditions in the embodiments of the present invention are performed according to the technical means commonly used in the art or the conditions recommended by the manufacturer.

Embodiment 1

A Sanxan gum synthetic strain-*Sphingomonas* sp. with a molecular marker has a deposit number of CGMCC No. 19480, Latin name of *Sphingomonas* sp., and the molecular marker is a nucleotide sequence shown in SEQ ID NO:1.

The application of the Sanxan gum synthetic strain-*Sphingomonas* sp. with a molecular marker in Sanxan gum preparation, includes the steps of:

A, inoculating the *Sphingomonas* sp. strain (CGMCC No. 19480) into a culture medium containing a carbon source and a nitrogen source after sterilization;

B, performing aeration fermentation at 28° C. until fermentation broth viscosity is not less than 3000 cp, and residual sugar does not exceed 0.3%;

C, performing extraction of the fermentation broth, solid-liquid separation, neutralization, drying and crushing to obtain the Sanxan gum.

In the step A, the carbon source in the culture medium is selected from sucrose, and the nitrogen source is selected from peptone.

In the step A, the *Sphingomonas* sp. strain (CGMCC No. 19480) is inoculated into the culture medium in a fermentation tank with an inoculation amount in which the volume percentage of the seed liquid and the culture medium is 10%-20%.

The culture medium in the step A is composed of the following components in mass percentage: carbon source 40%; nitrogen source 3%; magnesium sulfate 1%; dipotassium hydrogen phosphate 3%; soluble ferrous salt 3 ppm; calcium carbonate 1%; GPe 0.3%; and water as balance, pH=7.0-7.2.

In the step A, the *Sphingomonas* sp. strain (CGMCC No. 19480) after amplification culture is inoculated into the culture medium with an inoculation amount in which the volume percentage of the seed liquid and the culture medium is 10%.

The amplification culture process including the steps of:

(1) inoculating the *Sphingomonas* sp. strain (CGMCC No. 19480) into a first-class seed culture medium to obtain first-class seeds by aeration culture;

(2) performing amplification culture of the first-class seeds to obtain second-class seeds;

(3) inoculating the second-class seeds into the culture medium with an inoculation amount in which the volume percentage of the second-class seeds and the fermentation culture medium is 10%-20% to perform aeration fermentation.

The process conditions for obtaining the first-class seeds in the step (1) of the amplification culture process are as follows: inoculating an agarslant strain into the sterile first-class seed culture medium according to an inoculation amount of 0.5% mass ratio, performing aeration culture to obtain the first-class seeds under conditions of culture temperature of 28° C., aeration volume of 0.4 vvm, and seed age of 20 hours. The conditions for seed transmitting are *bacillus* strain, irregular arrangement and no pollution under microscopic examination.

An agarslant strain culture medium per liter includes the following components: 1.2 g sucrose; 0.25 g peptone; 0.25 g dipotassium hydrogen phosphate; 0.15 g yeast powder; 0.15 g diammonium hydrogen phosphate; 0.01 g magnesium sulfate; and 20 g agar; pH=7.0-7.2.

The first-class seed culture medium per liter includes the following components: 10 g carbon source; 5 g nitrogen source; 1 g magnesium sulfate; 3 g dipotassium hydrogen phosphate; 3 ppm soluble ferrous salt; and 0.3 g GPe; pH=7.0-7.2, where the carbon source is selected from sucrose, and the nitrogen source is selected from peptone.

A second-class seed culture medium in the step (2) of the amplification culture process includes the following components: 10 g carbon source; 5 g nitrogen source; 1 g magnesium sulfate; 3 g dipotassium hydrogen phosphate; 3 ppm soluble ferrous salt; and 0.3-0.5 g GPe; pH=7.0-7.2, wherein the carbon source is selected from sucrose; and the nitrogen source is selected from peptone.

The first-class seeds are inoculated into the sterile second-class seed culture solution with an inoculation amount in which the volume percentage of the first-class seeds and the second-class seed culture solution is 10%. The first-class seeds are cultured in the sterile second-class seed culture solution to obtain the second-class seeds under conditions of culture temperature of 28° C., aeration volume of 0.4 vvm, and seed age of 20 hours. The conditions for seed transmitting are *bacillus* strain, irregular arrangement and no pollution under microscopic examination.

The second-class seed culture solution is composed of the following components in mass percentage: glucose 2.5%; maltose 1.5%; soy powder 0.8%; ammonium sulfate 0.2%; and sterile water as balance; pH=7.0-7.3.

The first-class seeds are inoculated into the sterile second-class seed culture solution with an inoculation amount in which the volume percentage of the first-class seeds and the second-class seed culture solution is 12%-18%. The first-class seeds are cultured to obtain the second-class seeds under conditions of culture temperature of 30° C., aeration volume of 0.9 vvm, and culture period of 8 hours.

The aeration volume in the step B is 0.60 vvm.

The detection method of the fermentation broth viscosity in the step B includes:

(1) taking about 50 mL of the fermentation broth, removing its surface and stirring with a glass rod for 2-3 turns;

(2) correcting the leveling of a viscometer: adjusting a screw in its foot to make sure the viscometer is level;

(3) installing a rotor: installing a No. 4 rotor by turning it slightly;

(4) placing a beaker containing the fermentation broth on a lifting platform directly below the rotor, adjusting the lifting platform so that the liquid level of the fermentation broth reaches the scale of the rotor;

(5) turning on the power switch of the viscometer, adjusting the speed of the viscometer to 60 rpm, and reading the value after stabilization, where the viscosity=value×100.

The extraction step in the step C includes adding acid to adjust pH of the fermentation broth to 1.5, rising the temperature to 60° C. and maintaining for 30 minutes; where the acid is hydrochloric acid with a volume percentage concentration of 10%.

The neutralization step in the step C includes adding fibrous materials to sodium carbonate so that the pH of the materials after neutralization is 6.5-7.5, and the materials after neutralization is uniform and no particles.

Embodiment 2

The difference between the embodiment and the embodiment 1 is as follows.

The application of the Sanxan gum synthetic strain-*Sphingomonas* sp. with a molecular marker in Sanxan gum preparation, includes the steps of:

A, inoculating the *Sphingomonas* sp. strain (CGMCC No. 19480) into a culture medium containing a carbon source and a nitrogen source after sterilization;

B, performing aeration fermentation at 32° C. until fermentation broth viscosity is not less than 3000 cp, and residual sugar does not exceed 0.3%;

C, performing extraction of the fermentation broth, solid-liquid separation, neutralization, drying and crushing to obtain the Sanxan gum.

In the step A, the carbon source in the culture medium is selected from glucose, and the nitrogen source is selected from yeast extract.

In the step A, the *Sphingomonas* sp. strain (CGMCC No. 19480) is inoculated into the culture medium in a fermentation tank with an inoculation amount in which the volume percentage of the seed liquid and the culture medium is 20%.

The culture medium in the step A is composed of the following components in mass percentage: carbon source 60%; nitrogen source 5%; magnesium sulfate 2%; dipotassium hydrogen phosphate 4%; soluble ferrous salt 5 ppm; calcium carbonate 3%; GPe 0.5%; and water as balance, pH=7.0-7.2.

In the step A, the *Sphingomonas* sp. strain (CGMCC No. 19480) after amplification culture is inoculated into the culture medium with an inoculation amount in which the volume percentage of the seed liquid and the culture medium is 20%.

The amplification culture process including the steps of:

(1) inoculating the *Sphingomonas* sp. strain (CGMCC No. 19480) into a first-class seed culture medium to obtain first-class seeds by aeration culture;

(2) performing amplification culture of the first-class seeds to obtain second-class seeds;

(3) inoculating the second-class seeds into the culture medium with an inoculation amount in which the volume percentage of the second-class seeds and the fermentation culture medium is 20% to perform aeration fermentation.

The process conditions for obtaining the first-class seeds in the step (1) of the amplification culture process are as follows: inoculating an agarslant strain into a sterile first-class seed culture medium according to an inoculation amount of 0.8% mass ratio, performing aeration culture to obtain the first-class seeds under conditions of culture temperature of 32° C., aeration volume of 0.6 vvm, and seed age of 24 hours. The conditions for seed transmitting are *bacillus* strain, irregular arrangement and no pollution under microscopic examination.

The first-class seed culture medium per liter includes the following components: 15 g carbon source; 8 g nitrogen source; 2 g magnesium sulfate; 4 g dipotassium hydrogen phosphate; 5 ppm soluble ferrous salt; and 0.5 g GPe; pH=7.0-7.2, wherein the carbon source is selected from glucose, and the nitrogen source is selected from yeast extract.

A second-class seed culture medium in the step (2) of the amplification culture process includes the following components: 15 g carbon source; 8 g nitrogen source; 2 g magnesium sulfate; 4 g dipotassium hydrogen phosphate; 5 ppm soluble ferrous salt; 0.5 g GPe; pH=7.0-7.2, wherein the carbon source is selected from glucose; and the nitrogen source is selected from yeast extract.

The first-class seeds are inoculated into the sterile second-class seed culture solution with an inoculation amount in which the volume percentage of the first-class seeds and the second-class seed culture solution is 20%. The first-class seeds are cultured in the sterile second-class seed culture solution to obtain the second-class seeds under conditions of culture temperature of 30° C., aeration volume of 0.6 vvm, and seed age of 24 hours. The conditions for seed transmitting are *bacillus* strain, irregular arrangement and no pollution under microscopic examination.

The second-class seed culture solution is composed of the following components in mass percentage: glucose 2.8%; maltose 2.0%; soy powder 1.0%; ammonium sulfate 0.3%; and sterile water as balance; pH=7.0-7.3.

The first-class seeds are inoculated into the sterile second-class seed culture solution with an inoculation amount in which the volume percentage of the first-class seeds and the second-class seed culture solution is 18%. The first-class seeds are cultured in the sterile second-class seed culture solution to obtain the second-class seeds under conditions of culture temperature of 32° C., aeration volume of 1.0 vvm, and culture period of 10 hours.

The aeration volume in the step B is 1.0 vvm.

The extraction step in the step C includes adding acid to adjust pH of the fermentation broth to 2.0, rising the temperature to 80° C. and maintaining for 50 minutes; where the acid is sulfuric acid with a volume percentage concentration of 10%.

The neutralization step in the step C includes adding fibrous materials to sodium hydroxide so that the pH of the materials after neutralization is 6.5-7.5, and the materials after neutralization is uniform and no particles.

The rest is as mentioned above.

Embodiment 3

The difference between the embodiment and the embodiment 1 is as follows.

The application of the Sanxan gum synthetic strain-*Sphingomonas* sp. with a molecular marker in Sanxan gum preparation, includes the steps of:

A, inoculating the *Sphingomonas* sp. strain (CGMCC No. 19480) into a culture medium containing a carbon source and a nitrogen source after sterilization;

B, performing aeration fermentation at 30° C. until fermentation broth viscosity is not less than 3000 cp, and residual sugar does not exceed 0.3%;

C, performing extraction of the fermentation broth, solid-liquid separation, neutralization, drying and crushing to obtain the Sanxan gum.

In the step A, the carbon source in the culture medium is selected from corn powdered sugar, and the nitrogen source is selected from sodium nitrate.

In the step A, the *Sphingomonas* sp. strain (CGMCC No. 19480) is inoculated into the culture medium in a fermentation tank with an inoculation amount in which the volume percentage of the seed liquid and the culture medium is 15%.

The culture medium in the step A is composed of the following components in mass percentage: carbon source 50%; nitrogen source 4%; magnesium sulfate 1.5%; dipotassium hydrogen phosphate 3.5%; soluble ferrous salt 4 ppm; calcium carbonate 2%; GPe 0.4%; and water as balance, pH=7.0-7.2.

In the step A, the *Sphingomonas* sp. strain (CGMCC No. 19480) after amplification culture is inoculated into the culture medium with an inoculation amount in which the volume percentage of the seed liquid and the culture medium is 15%.

The amplification culture process including the steps of:

(1) inoculating the *Sphingomonas* sp. strain (CGMCC No. 19480) into a first-class seed culture medium to obtain first-class seeds by aeration culture;

(2) performing amplification culture of the first-class seeds to obtain second-class seeds;

(3) inoculating the second-class seeds into the culture medium with an inoculation amount in which the volume percentage of the second-class seeds and the fermentation culture medium is 15% to perform aeration fermentation.

The process conditions for obtaining the first-class seeds in the step (1) of the amplification culture process are as follows: inoculating an agarslant strain into the sterile first-class seed culture medium according to an inoculation amount of 0.65% mass ratio, performing aeration culture to obtain the first-class seeds under conditions of culture temperature of 30° C., aeration volume of 0.5 vvm, and seed age of 22 hours. The conditions for seed transmitting are *bacillus* strain, irregular arrangement and no pollution under microscopic examination.

The first-class seed culture medium per liter includes the following components: 13 g carbon source; 6.5 g nitrogen source; 1.5 g magnesium sulfate; 3.5 g dipotassium hydrogen phosphate; 4 ppm soluble ferrous salt; and 0.4 g GPe; pH=7.0-7.2, where the carbon source is selected from corn powdered sugar, and the nitrogen source is selected from sodium nitrate.

A second-class seed culture medium in the step (2) of the amplification culture process includes the following components: 13 g carbon source; 6.5 g nitrogen source; 1.5 g magnesium sulfate; 3.5 g dipotassium hydrogen phosphate; 4 ppm soluble ferrous salt; 0.4 g GPe; pH=7.0-7.2, where the carbon source is selected from corn powdered sugar; and the nitrogen source is selected from sodium nitrate.

The first-class seeds are inoculated into the sterile second-class seed culture solution with an inoculation amount in which the volume percentage of the first-class seeds and the second-class seed culture solution is 15%. The first-class seeds are cultured in the sterile second-class seed culture solution to obtain the second-class seeds under conditions of culture temperature of 29° C., aeration volume of 0.5 vvm, and seed age of 22 hours. The conditions for seed transmitting are *bacillus* strain, irregular arrangement and no pollution under microscopic examination.

The second-class seed culture solution is composed of the following components in mass percentage: glucose 2.7%; maltose 1.7%; soy powder 0.9%; ammonium sulfate 0.25%; and sterile water as balance; pH=7.0-7.3.

The first-class seeds are inoculated into the sterile second-class seed culture solution with an inoculation amount in which the volume percentage of the first-class seeds and the second-class seed culture solution is 15%. The first-class seeds are cultured in the sterile second-class seed culture solution to obtain the second-class seeds under conditions of culture temperature of 31° C., aeration volume of 0.95 vvm, and culture period of 9 hours.

The aeration volume in the step B is 0.8 vvm.

The extraction step in the step C includes adding acid to adjust pH of the fermentation broth to 1.7, rising the temperature to 70° C. and maintaining for 40 minutes; where the acid is chloroacetic acid with a volume percentage concentration of 10%.

The neutralization step in the step C includes adding fibrous materials to potassium hydroxide so that the pH of the materials after neutralization is 6.5-7.5, and the materials after neutralization is uniform and no particles.

The rest is as mentioned above.

Embodiment 4

The difference between the embodiment and the embodiment 1 is as follows.

The application of the Sanxan gum synthetic strain-*Sphingomonas* sp. with a molecular marker in Sanxan gum preparation, includes the steps of:

A, inoculating the *Sphingomonas* sp. strain (CGMCC No. 19480) into a culture medium containing a carbon source and a nitrogen source after sterilization;

B, performing aeration fermentation at 29° C. until fermentation broth viscosity is not less than 3000 cp, and residual sugar does not exceed 0.3%;

C, performing extraction of the fermentation broth, solid-liquid separation, neutralization, drying and crushing to obtain the Sanxan gum.

In the step A, the carbon source in the culture medium is selected from corn starch hydrolyzed sugar, and the nitrogen source is selected from ammonium chloride.

In the step A, the *Sphingomonas* sp. strain (CGMCC No. 19480) is inoculated into the culture medium in a fermentation tank with an inoculation amount in which the volume percentage of the seed liquid and the culture medium is 13%.

The culture medium in the step A is composed of the following components in mass percentage: carbon source 45%; nitrogen source 3.5%; magnesium sulfate 1.2%; dipotassium hydrogen phosphate 3.2%; soluble ferrous salt 3.5 ppm; calcium carbonate 1.5%; GPe 0.35%; and water as balance, pH=7.0-7.2.

In the step A, the *Sphingomonas* sp. strain (CGMCC No. 19480) after amplification culture is inoculated into the culture medium with an inoculation amount in which the volume percentage of the seed liquid and the culture medium is 13%.

The amplification culture process including the steps of:

(1) inoculating the *Sphingomonas* sp. strain (CGMCC No. 19480) into a first-class seed culture medium to obtain first-class seeds by aeration culture;

(2) performing amplification culture of the first-class seeds to obtain second-class seeds;

(3) inoculating the second-class seeds into the culture medium with an inoculation amount in which the volume percentage of the second-class seeds and the fermentation culture medium is 13% to perform aeration fermentation.

The process conditions for obtaining the first-class seeds in the step (1) of the amplification culture process are as follows: inoculating an agarslant strain into the sterile first-class seed culture medium according to an inoculation amount of 0.55% mass ratio, performing aeration culture to obtain the first-class seeds under conditions of culture temperature of 29° C., aeration volume of 0.45 vvm, and seed age of 21 hours. The conditions for seed transmitting are *bacillus* strain, irregular arrangement and no pollution under microscopic examination.

The first-class seed culture medium per liter includes the following components: 11 g carbon source; 5.5 g nitrogen source; 1.2 g magnesium sulfate; 3.2 g dipotassium hydrogen phosphate; 3.5 ppm soluble ferrous salt; and 0.35 g GPe; pH=7.0-7.2, where the carbon source is selected from starch hydrolyzed sugar, and the nitrogen source is selected from ammonium chloride.

A second-class seed culture medium in the step (2) of the amplification culture process includes the following components: 15 g carbon source; 5.5 g nitrogen source; 1.2 g magnesium sulfate; 3.2 g dipotassium hydrogen phosphate; 3. ppm soluble ferrous salt; 0.35 g GPe; pH=7.0-7.2, where the carbon source is selected from starch hydrolyzed sugar; and the nitrogen source is selected from ammonium chloride.

The first-class seeds are inoculated into the sterile second-class seed culture solution with an inoculation amount in which the volume percentage of the first-class seeds and the second-class seed culture solution is 12%. The first-class seeds are cultured in the sterile second-class seed culture solution to obtain the second-class seeds under conditions of culture temperature of 28° C., aeration volume of 0.45 vvm, and seed age of 21 hours. The conditions for seed transmitting are *bacillus* strain, irregular arrangement and no pollution under microscopic examination.

The second-class seed culture solution is composed of the following components in mass percentage: glucose 2.55%; maltose 1.6%; soy powder 0.85%; ammonium sulfate 0.22%; and sterile water as balance; pH=7.0-7.3.

The first-class seeds are inoculated into the sterile second-class seed culture solution with an inoculation amount in which the volume percentage of the first-class seeds and the second-class seed culture solution is 13%. The first-class seeds are cultured to obtain the second-class seeds under conditions of culture temperature of 30° C., aeration volume of 0.92 vvm, and culture period of 8.5 hours.

The aeration volume in the step B is 0.7 vvm.

The extraction step in the step C includes adding acid to adjust pH of the fermentation broth to 1.5-2.0, rising the temperature to 65° C. and maintaining for 35 minutes; where the acid is a mixture of hydrochloric acid and sulfuric acid with a volume percentage concentration of 10%.

The neutralization step in the step C includes adding fibrous materials to a mixture of sodium carbonate and sodium hydroxide so that the pH of the materials after neutralization is 6.5-7.5, and the materials after neutralization is uniform and agranular.

The rest is as mentioned above.

Embodiment 5

The difference between the embodiment and the embodiment 1 is as follows:

The application of the Sanxan gum synthetic strain-*Sphingomonas* sp. with a molecular marker in Sanxan gum preparation, includes the steps of:

A, inoculating the *Sphingomonas* sp. strain (CGMCC No. 19480) into a culture medium containing a carbon source and a nitrogen source after sterilization;

B, performing aeration fermentation at 31° C. until fermentation broth viscosity is not less than 3000 cp, and residual sugar does not exceed 0.3%;

C, performing extraction of the fermentation broth, solid-liquid separation, neutralization, drying and crushing to obtain the Sanxan gum.

In the step A, the carbon source in the culture medium is a mixture of sucrose and glucose, and the nitrogen source is a mixture of peptone and sodium nitrate.

In the step A, the *Sphingomonas* sp. strain (CGMCC No. 19480) is inoculated into the culture medium in a fermentation tank with an inoculation amount in which the volume percentage of the seed liquid and the culture medium is 18%.

The culture medium in the step A is composed of the following components in mass percentage: carbon source 55%; nitrogen source 4.5%; magnesium sulfate 1.8%; dipotassium hydrogen phosphate 3.8%; soluble ferrous salt 4.5 ppm; calcium carbonate 2.5%; GPe 0.45%; and water as balance, pH=7.0-7.2.

In the step A, the *Sphingomonas* sp. strain (CGMCC No. 19480) after amplification culture is inoculated into the culture medium with an inoculation amount in which the volume percentage of the seed liquid and the culture medium is 18%.

The amplification culture process including the steps of:

(1) inoculating the *Sphingomonas* sp. strain (CGMCC No. 19480) into a first-class seed culture medium to obtain first-class seeds by aeration culture;

(2) performing amplification culture of the first-class seeds to obtain second-class seeds;

(3) inoculating the second-class seeds into the culture medium with an inoculation amount in which the volume percentage of the second-class seeds and the fermentation culture medium is 18% to perform aeration fermentation.

The process conditions for obtaining the first-class seeds in the step (1) of the amplification culture process are as follows: inoculating an agarslant strain into the sterile first-class seed culture medium according to an inoculation amount of 0.7% mass ratio, performing aeration culture to obtain the first-class seeds under conditions of culture temperature of 31° C., aeration volume of 0.55 vvm, and seed age of 23 hours. The conditions for seed transmitting are *bacillus* strain, irregular arrangement and no pollution under microscopic examination.

The first-class seed culture medium per liter includes the following components: 14 g carbon source; 7 g nitrogen source; 1.8 g magnesium sulfate; 3.8 g dipotassium hydrogen phosphate; 4.5 ppm soluble ferrous salt; and 0.45 g GPe; pH=7.0-7.2, where the carbon source is a mixture of sucrose and glucose, and the nitrogen source is a mixture of a mixture of peptone and sodium nitrate.

A second-class seed culture medium in the step (2) of the amplification culture process includes the following components: 14 g carbon source; 7 g nitrogen source; 1.8 g magnesium sulfate; 3.8 g dipotassium hydrogen phosphate; 4.5 ppm soluble ferrous salt; 0.45 g GPe; pH=7.0-7.2, where the carbon source is a mixture of sucrose and glucose; and the nitrogen source is a mixture of peptone and sodium nitrate.

The first-class seeds are inoculated into the sterile second-class seed culture solution with an inoculation amount in which the volume percentage of the first-class seeds and the second-class seed culture solution is 18%. The first-class seeds are cultured in the sterile second-class seed culture solution to obtain the second-class seeds under conditions of culture temperature of 30° C., aeration volume of 0.55 vvm, and seed age of 23 hours. The conditions for seed transmitting are *bacillus* strain, irregular arrangement and no pollution under microscopic examination.

The second-class seed culture solution is composed of the following components in mass percentage: glucose 2.7%; maltose 1.9%; soy powder 0.95%; ammonium sulfate 0.28%; and sterile water as balance; pH=7.0-7.3.

The first-class seeds are inoculated into the sterile second-class seed culture solution with an inoculation amount in which the volume percentage of the first-class seeds and the second-class seed culture solution is 17%. The first-class seeds are cultured to obtain the second-class seeds under conditions of culture temperature of 32° C., aeration volume of 0.98 vvm, and culture period of 9.5 hours.

The aeration volume in the step B is 0.9 vvm.

The extraction step in the step C includes adding acid to adjust pH of the fermentation broth to 1.5-2.0, rising the temperature to 75° C. and maintaining for 45 minutes; where the acid is a mixture of sulfuric acid and chloroacetic acid with a volume percentage concentration of 10%.

The neutralization step in the step C includes adding fibrous materials to a mixture of sodium carbonate and potassium hydroxide so that the pH of the materials after neutralization is 6.5-7.5, and the materials after neutralization is uniform and agranular.

The rest is as mentioned above.

Embodiment 6

Fermentation broth of the *Sphingomonas* sp. strain (CGMCC No. 19480) is centrifuged at 10000 rpm for 15 minutes to collect strain cells, genomic DNA extraction is performed with a bacterial genomic DNA extraction kit from Tiangen Biotech (Beijing) Co., Ltd., and PCR amplification is performed using a primer 1 (5'-TCAGGCCGTGTGGG-GAA-3', SEQ ID NO: 2) and a primer 1 (5'-GATCC-GATCCAGCTTTCG GG-3', SEQ ID NO: 3) as primers. The PCR amplification system comprises 1 μL of 10-30 ng/μL template DNA, 0.5 μL upstream primer, 0.5 μL downstream primer, 1.0 μL of 10 mM dNTP, 2.5 μL of 10× buffer, 0.5 μL of 5 U/μL Platinum Taq DNA polymerase, with adding water up to 25 μL in sum. The PCR amplification conditions are as follow: pre-denaturation at 95° C. for 5 minutes; 94° C. for 45 seconds, 62° C. for 45 seconds, 72° C. for 1 minute, 30 cycles; 72° C. extension for 10 minutes. 5 μL of the PCR amplification product is mixed with 1 μL of loading buffer, sampled into a 1.5% agarose gel, subjected to electrophoresis, and stained with GoldView nucleic acid dye for 10 minutes. A PCR amplification band about 950 bp is observed. The PCR amplification product is subjected to DNA sequencing in Beijing Aoke Dingsheng Biotechnology Co., Ltd. to obtain the following sequence (SEQ ID NO: 1):

```
ACGGCAGGACCTCGCCTTGCAGCAGCCGCGTCGCCTGGCG

ACGGTCGAGCGCGCGCGAGAAGAGGAAGCCTTGGCCATATTTG

CAGCCATAGCGCTGCAGCAGCCGGCACTGCGCCTCCGTCTCGA

TTCCCTCGGCGACGACCCGCAGCTTGAGACCGTCGGCAATCGC

GATCAGCCCCTGCACGATCGCAGCGCTGCCCGCATCGGTGCCG

AGCTGCTGGACGAAGGAGCGGTCGATCTTGATGATGTCCACCG
```

```
GCACCGAGAGCAGGTGCGTCAGCGAGGCATAGCCGGTACCGA

AATCGTCGAGCGCGATGCGGAGCCCGCGCGCCTGCAATCCTTC

GAGAACGCGGCGCACGGTATCGGCGCGCCGGTCCATATGGACC

GTCTCGGTCACTTCGACGACCAGATGGCCGAGCGGCACGCGGG

CATGCTCGAACGTGTCGGCCAGCGTGCGTTCGAGCAGGCCGCC

GCCATGGATGTCGGCGGAGCCGACGTTGATCGAGATCTGCGGA

TCGGCGATGCCCAGCCGCATCCAGTGCGCGATGTCGCCGGCGA

CGATCCTCAGCATCCGTCGCGTGAGTTCCGGGGCGATGCGCGG

GTGCGACATCGCTTGGTGGAAGGCGGCGGCCGGCAGCACTTCG

CCCGTGGACGTCGTCAGGCGGCAGAGCGCCTCGAACGACGTTA

CCGCCCATGTCTCCAGTTCGACGACCGGCTGATAATAGGCGTCG

ATACGATCTTCGTGCAGTGCGCGCTCAAGATCGTGCAACGCGTC

GGGATGGCTCGCCACCGCATTGCCCAGGCTCGCGGAATAAGCG

AGGTGGCCGCCGCGGTGCGACTGCTTGGCGTGCTGCAGCGCAT

TGGTGGCATGTTCGAACAGAATGTCGGACGTCTTCGCCGGATC

GCTGATCGCAAAGCCGATG
```

The product performances and the gum yields of products in Embodiments 1-5 are detected by the Applicant, and the results are as follows:

| | Embodiment 1 | Embodiment 2 | Embodiment 3 | Embodiment 4 | Embodiment 5 |
|---|---|---|---|---|---|
| Viscosity of 1% KCl solution (25° C.)/MPa·s | 1650 | 1700 | 1650 | 1800 | 1650 |
| Viscosity of 0.25% synthetic brine (25° C.)/MPa·s | 550 | 600 | 550 | 700 | 550 |
| Viscosity of 1% aqueous solution (25° C.)/MPa·s | 950 | 1000 | 950 | 1000 | 950 |
| Gel strength (g/cm$^2$) | 30 | 35 | 30 | 35 | 30 |
| 0.175 mm bore diameter sieve particle size (%) | 96 | 96 | 97 | 96 | 96 |
| Whiteness | 47 | 47 | 51 | 50 | 48 |
| Gum yield (%) | 3.01 | 3.21 | 3.4 | 3.08 | 3.2 |

It is not difficult to see from the above comparison that the viscosity of 1% KCl solution of the Sanxan gum, viscosity of 0.25% synthetic brine of the Sanxan gum, viscosity of 1% aqueous solution of the Sanxan gum, gel strength of the Sanxan gum, and gum yield of the Sanxan gum of any of Embodiments 1-5 of the present invention are much better than existing processes and products.

What is claimed is:

1. A method for identifying a Sanxan gum producing-strain-*Sphingomonas* sp comprising a step of identifying the Sanxan gum producing strain-*Sphingomonas* sp. with a molecular marker; wherein the Sanxan gum producing strain-*Sphingomonas* sp. is *Sphingomonas* sp. strain NW20200301 deposited under CGMCC Accession Number: 19480 in the China General Microbiological Culture Collection Center, the molecular marker is a nucleotide having the nucleotide sequence shown in SEQ ID NO. 1.

2. The method according to claim 1, being characterized in that, it comprises the following steps of:

A, inoculating the *Sphingomonas* sp. strain (CGMCC No. 19480) into a culture medium containing a carbon source and a nitrogen source after sterilization;

B, performing aeration fermentation at 28-32° C. until fermentation broth viscosity is not less than 3000 cp, and residual sugar does not exceed 0.3%;

C, performing extraction of the fermentation broth, solid-liquid separation, neutralization, drying and crushing to obtain the Sanxan gum.

3. The method according to claim 2, being characterized in that, the carbon source in the culture medium of the step A is selected from one or any combination of sucrose, glucose, corn powdered sugar, and starch hydrolyzed sugar; and the nitrogen source is selected from one or any combination of peptone, yeast extract, sodium nitrate, ammonium chloride, and ammonium sulfate.

4. The method according to claim 2, being characterized in that, in the step A, the *Sphingomonas* sp. strain (CGMCC No. 19480) is inoculated into the culture medium in a fermentation tank with an inoculation amount in which the volume percentage of the seed liquid and the culture medium is 10%-20%.

5. The method according to claim 2, being characterized in that, the culture medium in the step A is composed of the following components in mass percentage:
carbon source 40%-60%; nitrogen source 3%-5%; magnesium sulfate 1%-2%; dipotassium hydrogen phosphate 3%-4%; soluble ferrous salt 3-5 ppm; calcium carbonate 1%-3%; GPe 0.3%-0.5%; and water as balance, pH=7.0-7.2.

6. The method according to claim 3, being characterized in that, the culture medium in the step A is composed of the following components in mass percentage:
carbon source 40%-60%; nitrogen source 3%-5%; magnesium sulfate 1%-2%; dipotassium hydrogen phosphate 3%-4%; soluble ferrous salt 3-5 ppm; calcium carbonate 1%-3%; GPe 0.3%-0.5%; and water as balance, pH=7.0-7.2.

7. The method according to claim 4, being characterized in that, the culture medium in the step A is composed of the following components in mass percentage:
carbon source 40%-60%; nitrogen source 3%-5%; magnesium sulfate 1%-2%; dipotassium hydrogen phosphate 3%-4%; soluble ferrous salt 3-5 ppm; calcium carbonate 1%-3%; GPe 0.3%-0.5%; and water as balance, pH=7.0-7.2.

8. The method according to claim 2, being characterized in that, in the step A, the *Sphingomonas* sp. strain (CGMCC No. 19480) after amplification culture is inoculated into the culture medium with an inoculation amount in which the volume percentage of the seed liquid and the culture medium is 10%-20%.

9. The method according to claim 8, being characterized in that, the amplification culture process comprising the steps of:
(1) inoculating the *Sphingomonas* sp. strain (CGMCC No. 19480) into a first-class seed culture medium to obtain first-class seeds by aeration culture;
(2) performing amplification culture of the first-class seeds to obtain second-class seeds;
(3) inoculating the second-class seeds into the culture medium with an inoculation amount in which the volume percentage of the second-class seeds and the fermentation culture medium is 10%-20% to perform aeration fermentation.

10. The method according to claim 9, being characterized in that, the process conditions for obtaining the first-class seeds in the step 1) of the amplification culture process comprises: inoculating an agarslant strain into a sterile first-class seed culture medium according to an inoculation amount of 0.5%-0.8% mass ratio, performing aeration culture to obtain the first-class seeds under conditions of culture temperature of 28-32° C., ventilation volume of 0.4 vvm-0.6 vvm, and seed age of 20-24 hours, and the conditions for seed transmitting being *bacillus* strain, irregular arrangement and no pollution under microscopic examination;
an agarslant strain culture medium per liter comprising the following components: 1.2 g sucrose; 0.25 g peptone; 0.25 g dipotassium hydrogen phosphate; 0.15 g yeast powder; 0.15 g diammonium hydrogen phosphate; 0.01 g magnesium sulfate; and 20 g agar; pH=7.0-7.2;
the first-class seed culture medium per liter comprising the following components: 10-15 g carbon source; 5-8 g nitrogen source; 1-2 g magnesium sulfate; 3-4 g dipotassium hydrogen phosphate; 3-5 ppm soluble ferrous salt; and 0.3-0.5 g GPe; pH=7.0-7.2, wherein the carbon source is selected from one or any combination of sucrose, glucose, corn powdered sugar, and starch hydrolyzed sugar; and the nitrogen source is selected from one or any combination of peptone, yeast extract, sodium nitrate, ammonium chloride, and ammonium sulfate.

11. The method according to claim 9, being characterized in that, a second-class seed culture medium in the step 2) of the amplification culture process comprises the following components:
10-15 g carbon source; 5-8 g nitrogen source; 1-2 g magnesium sulfate; 3-4 g dipotassium hydrogen phosphate; 3-5 ppm soluble ferrous salt; and 0.3-0.5 g GPe; pH=7.0-7.2;
wherein the carbon source is selected from one or any combination of sucrose, glucose, corn powdered sugar, and starch hydrolyzed sugar; and the nitrogen source is selected from one or any combination of peptone, yeast extract, sodium nitrate, ammonium chloride, and ammonium sulfate;
the first-class seeds being inoculated into the sterile second-class seed culture solution with an inoculation amount in which the volume percentage of the first-class seeds and the second-class seed culture solution is 10%-20%, the first-class seeds being cultured in the sterile second-class seed culture solution to obtain the second-class seeds under conditions of culture temperature of 28-30° C., ventilation volume of 0.4 vvm-0.6 vvm, and seed age of 20-24 hours, and the conditions for seed transmitting being *bacillus* strain, irregular arrangement and no pollution under microscopic examination.

12. The method according to claim 11, being characterized in that, the second-class seed culture solution is composed of the following components in mass percentage:
glucose 2.5%-2.8%; maltose 1.5%-2.0%; soy powder 0.8%-1.0%; ammonium sulfate 0.2%-0.3%; and sterile water as balance; pH=7.0-7.3;
the first-class seeds being inoculated into the sterile second-class seed culture is solution with an inoculation amount in which the volume percentage of the first-class seeds and the second-class seed culture solution is 12%-18%, the first-class seeds being cultured to obtain the second-class seeds under conditions of culture temperature of 30-32° C., ventilation volume of 0.9 vvm-1.0 vvm, and culture period of 8-10 hours.

13. The method according to claim 2, being characterized in that, the ventilation volume in the step B is 0.6-1.0 vvm.

14. The method according to claim 3, being characterized in that, a test for determining the fermentation broth viscosity in the step B comprises:
(1) taking about 50 mL of the fermentation broth, removing its surface and stirring with a glass rod for 2-3 turns;
(2) correcting the leveling of a viscometer: adjusting a screw in its foot to make sure the viscometer is level;
(3) installing a rotor: installing a No. 4 rotor by turning it slightly;
(4) placing a beaker containing the fermentation broth on a lifting platform directly below the rotor, adjusting the lifting platform so that the liquid level of the fermentation broth reaches the scale of the rotor;
(5) turning on the power switch of the viscometer, adjusting the speed of the viscometer to 60 rpm, and reading the value after stabilization, wherein the viscosity=value×100.

15. The method according to claim 2, being characterized in that, is the extraction step in the step C comprises adding acid to adjust pH of the fermentation broth to 1.5-2.0, rising the temperature to 60-80° C. and maintaining for 30-50 minutes; wherein the acid is one or any combination of hydrochloric acid, sulfuric acid, and chloroacetic acid with a volume percentage concentration of 10%.

16. The method according to claim 2, being characterized in that, the neutralization step in the step C comprises adding fibrous materials to one or a mixture of sodium carbonate, sodium hydroxide and potassium hydroxide so that the pH of the fibrous materials after neutralization is 6.5-7.5, and the fibrous materials after neutralization is uniform and agranular.

\* \* \* \* \*

SEQUENCE LISTING

<160> NUMBER OF SEQ ID NOS: 5

<210> SEQ ID NO 1
<211> LENGTH: 920
<212> TYPE: DNA
<213> ORGANISM: Sphingomonas sp. CGMCC19480

<400> SEQUENCE: 1

```
acggcaggac ctcgccttgc agcagccgcg tcgcctggcg acggtcgagc gcgcgcgaga      60
agaggaagcc ttggccatat ttgcagccat agcgctgcag cagccggcac tgcgcctccg     120
tctcgattcc ctcggcgacg acccgcagct tgagaccgtc ggcaatcgcg atcagcccct     180
gcacgatcgc agcgctgccc gcatcggtgc cgagctgctg gacgaaggag cggtcgatct     240
tgatgatgtc caccggcacc gagagcaggt gcgtcagcga ggcatagccg gtaccgaaat     300
cgtcgagcgc gatgcggagc ccgcgcgcct gcaatccttc gagaacgcgg cgcacggtat     360
cggcgcgccg gtccatatgg accgtctcgg tcacttcgac gaccagatgg ccgagcggca     420
cgcgggcatg ctcgaacgtg tcggccagcg tgcgttcgag caggccgccg ccatggatgt     480
cggcggagcc gacgttgatc gagatctgcg gatcggcgat gcccagccgc atccagtgcg     540
cgatgtcgcc ggcgacgatc ctcagcatcc gtcgcgtgag ttccggggcg atgcgcgggt     600
gcgacatcgc ttggtggaag gcggcggccg gcagcacttc gcccgtggac gtcgtcaggc     660
ggcagagcgc ctcgaacgac gttaccgccc atgtctccag ttcgacgacc ggctgataat     720
aggcgtcgat acgatcttcg tgcagtgcgc gctcaagatc gtgcaacgcg tcgggatggc     780
tcgccaccgc attgcccagg ctcgcggaat aagcgaggtg gccgccgcgg tgcgactgct     840
tggcgtgctg cagcgcattg gtggcatgtt cgaacagaat gtcggacgtc ttcgccggat     900
cgctgatcgc aaagccgatg                                                 920
```

```
<210> SEQ ID NO 2
<211> LENGTH: 17
<212> TYPE: DNA
<213> ORGANISM: Artificial Sequence
<220> FEATURE:
<223> OTHER INFORMATION: It is synthesized.

<400> SEQUENCE: 2
tcaggccgtg tggggaa                                                    17

<210> SEQ ID NO 3
<211> LENGTH: 20
<212> TYPE: DNA
<213> ORGANISM: Artificial Sequence
<220> FEATURE:
<223> OTHER INFORMATION: It is synthesized.

<400> SEQUENCE: 3
gatccgatcc agctttcggg                                                 20

<210> SEQ ID NO 4
<211> LENGTH: 261
<212> TYPE: DNA
<213> ORGANISM: Sphigomonas sp. CGMCC19480

<400> SEQUENCE: 4
cgcgcgcgag aagaggaagc cttggccata tttgcagcca tagcgctgca gcagccggca     60
ctgcgcctcc gtctcgattc cctcggcgac gacccgcagc ttgagaccgt cggcaatcgc    120
gatcagcccc tgcacgatcg cagcgctgcc cgcatcggtg ccgagctgct ggacgaagga    180
gcggtcgatc ttgatgatgt ccaccggcac cgagagcagg tgcgtcagcg aggcatagcc    240
ggtaccgaaa tcgtcgagcg c                                              261

<210> SEQ ID NO 5
<211> LENGTH: 261
<212> TYPE: DNA
<213> ORGANISM: Bosea vaviloviae

<400> SEQUENCE: 5
cgcgcgcgag tagagatagc cttggccaag gtggcagccg atcatctgca atcgctcgga     60
ctgcccttgc gtttcgattc cctcggcgat gaccttcatg ccgaggcggt tggcgatccc    120
gaccagcgcc tcgacgatca cgctgctcct ggcgccgctt tcgatgccgc cgacgaagga    180
gcggtcgatc ttgatgatgt cgaccgggaa atccagcaga tgcgtcagcg acgcgaagcc    240
ggtgccgaaa tcgtccagcg c                                              261
```